(12) United States Patent
Neubauer et al.

(10) Patent No.: US 7,043,326 B2
(45) Date of Patent: May 9, 2006

(54) METHOD OF MONITORING EXTENT OF CURE

(75) Inventors: Christopher M. Neubauer, Pittsburgh, PA (US); Jeffrey Niederst, Pittsburgh, PA (US); David M. Riddle, Irwin, PA (US); Jeffrey R. Kubala, Glenshaw, PA (US)

(73) Assignee: Valspar Sourcing, Inc., Minneapolis, MN (US)

(*) Notice: Subject to any disclaimer, the term of this patent is extended or adjusted under 35 U.S.C. 154(b) by 0 days.

(21) Appl. No.: 10/271,501

(22) Filed: Oct. 15, 2002

(65) Prior Publication Data

US 2003/0074095 A1    Apr. 17, 2003

Related U.S. Application Data

(60) Provisional application No. 60/330,135, filed on Oct. 16, 2001.

(51) Int. Cl.
*G06F 19/00* (2006.01)
*G01J 3/42* (2006.01)
*G01J 3/427* (2006.01)
*B05D 3/00* (2006.01)

(52) U.S. Cl. .................... 700/117; 356/319; 427/10

(58) Field of Classification Search ............... 700/90, 700/95, 108–110, 117, 123; 356/19, 319; 427/8–10, 385.5, 388.1, 388.2; 118/663–665, 118/668, 669, 688
See application file for complete search history.

(56) References Cited

U.S. PATENT DOCUMENTS

| | | | |
|---|---|---|---|
| 3,679,309 A | 7/1972 | Hiragaki et al. | |
| 3,974,678 A | 8/1976 | Rooney et al. | |
| 4,582,520 A | 4/1986 | Sturm | |
| 4,590,803 A | 5/1986 | Harrold | |
| 4,651,011 A | 3/1987 | Ors et al. | |
| 4,885,254 A | 12/1989 | Sung | |
| 4,922,113 A | 5/1990 | Melancon | |
| 5,037,763 A | 8/1991 | Petisce | |
| 5,047,444 A | 9/1991 | DeVoe et al. | |
| 5,118,559 A | 6/1992 | DeVoe et al. | |
| 5,142,151 A * | 8/1992 | Varnell et al. | ......... 250/339.08 |
| 5,158,720 A | 10/1992 | Levy | |
| 5,182,316 A | 1/1993 | DeVoe et al. | |
| 5,233,195 A | 8/1993 | Hellstrom et al. | |
| 5,281,819 A | 1/1994 | Keffert et al. | |
| 5,290,586 A * | 3/1994 | McDonnell Bushnell et al. | ............... 427/8 |
| 5,318,808 A * | 6/1994 | Crivello et al. | ............. 427/517 |

(Continued)

FOREIGN PATENT DOCUMENTS

EP    0 400 972 B1    12/1990

(Continued)

OTHER PUBLICATIONS

Palackdharry, P.; Wankegan, Dexter. "UV Absorbance Method for Coatings Cure Determination". Society of Manufacturing Engineers, v27, n3, pp. 1-12. 1992.*

(Continued)

*Primary Examiner*—Leo Picard
*Assistant Examiner*—Ryan Jarrett
(74) *Attorney, Agent, or Firm*—Shumaker & Sieffert, P.A.

(57) ABSTRACT

Method of measuring extent of cure of a coating comprising operating a metal-containing substrate coating operation to provide a coated metal-containing substrate; positioning an investigative apparatus near the coated metal-containing substrate; and operating the investigative apparatus to obtain an extent of cure reading, the reading corresponding to an area on the coated metal-containing substrate.

18 Claims, 6 Drawing Sheets

U.S. PATENT DOCUMENTS

| | | | |
|---|---|---|---|
| 5,418,369 | A | 5/1995 | Moore et al. |
| 5,457,539 | A | 10/1995 | Sturm |
| 5,556,663 | A | 9/1996 | Chang et al. |
| 5,598,005 | A | 1/1997 | Wang et al. |
| 5,606,171 | A * | 2/1997 | Neckers et al. .......... 250/459.1 |
| 5,627,372 | A | 5/1997 | Sturm |
| 5,633,313 | A | 5/1997 | Blanchard et al. |
| 5,707,587 | A | 1/1998 | Blanchard et al. |
| 5,717,217 | A | 2/1998 | Neckers et al. |
| 5,872,447 | A | 2/1999 | Hager, III |
| 5,955,002 | A | 9/1999 | Neckers et al. |
| 6,099,162 | A | 8/2000 | Walsh |
| 6,475,571 | B1 * | 11/2002 | Echigo et al. .............. 427/458 |

FOREIGN PATENT DOCUMENTS

| | | |
|---|---|---|
| WO | WO 86/07456 | 12/1986 |
| WO | WO97/23550 | 7/1997 |
| WO | WO 98/41316 | 9/1998 |

OTHER PUBLICATIONS

Bruckner, K.J.; Charalambous, G.; Hardwick, W.A. "IR Reflectance Spectra of Beer Can Coatings". Master Brewers Association of America. 9(1) pp. 47-53. 1972.*

Kern, P.; Baner, A.L.; Lange, J. "Electrochemical Impedance Spectroscopy as a Tool for Investigating the Quality and Performance of Coated Food Cans". The Journal of Coatings Technology, v71, n899, p. 67. Dec. 1999.* http://www.uvprocess.com—CON-TROL-CURE® Curing Control Products, UV Process Suppy, Inc., Copyright 200, 4 pages.

http://www.radtech.org/publications—Radtech 2000 Proceedings, Table of Contents, 6 pages.

http://www.sglinc.com/cure.htm—"Cure Monitoring Technology," Spectra Group Limited, Inc., 3 pages.

http://www.micromet.com/holometrix/m_main.asp—"Micromet Instruments," Holometrix® Micromet, A Metrisa Company, Copyright 2001.

http://www.nortest.co.uk/curpak.html—"CURE-PAK Through-Oven Analyser," Nortest, UK.

http://www.aps.org/BAPSMAR98/abs/S3650009.html—"Cure Monitoring of an Unsaturated Polyester Resin Using Near-Infrared and Fluorescence Spectroscopies," Session S8—Processing. Mixed Session, Mar. 19, Los Angeles Convention Center, 7 pages.

http://www.cranfield.ac.uk/sims/curenet—Curenet, UK-based, EPSRC sponsored, Engineering Programme Network on "Real Time Cure Monitoring in the Manufacture of Composites Structures," Published by Advanced Materials Department, Cranfield University, Copyright 1998, 1999.

http://ww-isl.stanford.edu/groups/MURI/annual98/node65.html—Photoresist Cure Monitoring, 1 page.

Anonymous, "Platen design to measure the gel times of epoxy resin varnishes—uses slots machined in top and bottom platen cariers," Abstract only, 1 page.

Bankowsky et al., "The principles of radiation curing," from www.radcure.net—3 pages.

Denney, "An introduction to UV curing and the UV inerted curing process," from www.radcure.net 8 pages.

Lenhart, "Probing The Structure of the Buried Epoxy / Coupling Agent / Glass Interfacial Region with an Immobilized Fluorescent Probe," A Dissertation submitted to The Johns Hopkins University, Apr. 2000, Baltimore, Maryland, Abstract only, 2 pages.

"Standard Practice for Assessing the Solvent Resistance of Organic Coatings Using Solvent Rubs," *Annual Book of ASTM Standards*, Designation D 5402-93, pp. 552-554.

"Standard Test Method for Calculation of Color Differences From Instrumentally Measured Color Coordinates," *Annual Book of ASTM Standards*, Designation D 2244-93 (Reapproved 2000), pp. 1-5.

"Standard Test Method for Porosity in Vitreous Whitewares by Dye Penetration," *Annual Book of ASTM Standards*, Designation C949-980 (Reapproved 2000), pp. 1-4.

"Standard Test Methods for Bend Testing of Material for Ductility," *Annual Book of ASTM Standards*, Designation: E 290-97a, 1998, pp. 1-7.

Willard et al., *Instrumental Methods of Analysis*, 7th Edition, Wadsworth Publishing Company, Belmont, California, Appendixes, pp. 860-865.

Zwanenburg, "How to formulate UV-curing coatings," from www.radcure.net—20 pages.

* cited by examiner

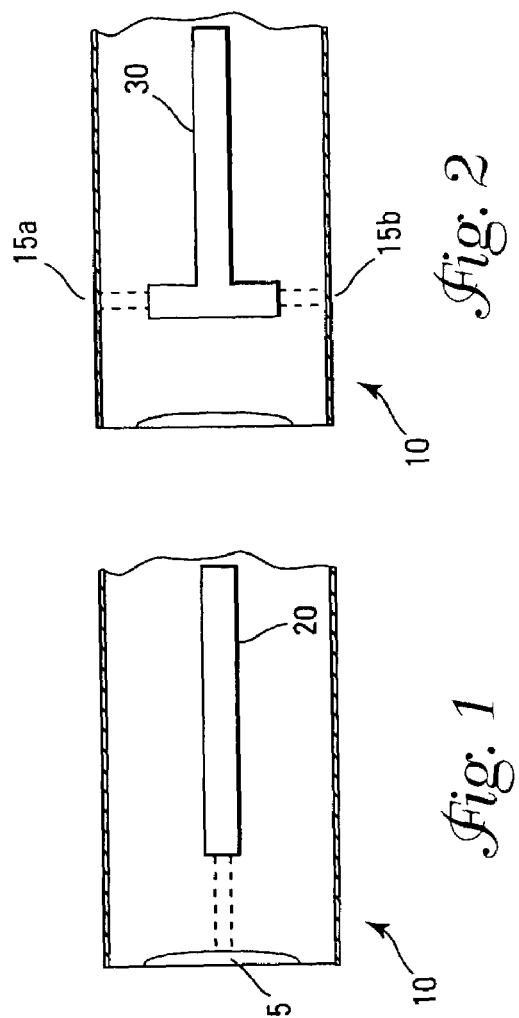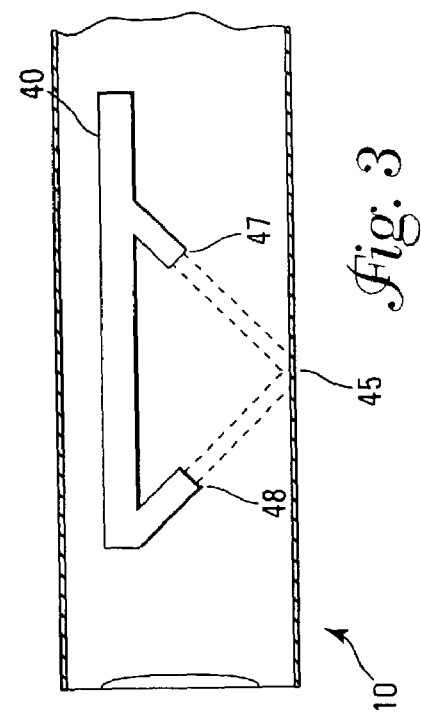

METHOD OF MONITORING EXTENT OF CURE

RELATED APPLICATIONS

This application claims priority from U.S. Provisional Application Ser. No. 60/330,135, filed Oct. 16, 2001.

FIELD OF THE INVENTION

The invention relates to methods of monitoring physical characteristics of a coating. In particular, the invention relates to methods of measuring, for example, the extent of cure of a coating, where such methods can be incorporated into a manufacturing operation.

BACKGROUND

Quality monitoring in manufacturing operations is generally used to ensure compliance with set standards. Systems and processes that incorporate quality control can provide high quality products and high yields, subsequently leading to increased efficiency.

In the food packaging industry, quality is often associated with how well containers perform. Containers that either hold, transport or store ingestible items are expected to perform or resist damage from a variety of internal and external conditions, and protect the foodstuff or liquid contained inside. Coatings are often applied to metal substrates to impart barrier properties, stain resistance, corrosion resistance, oxidation resistance and/or to enhance aesthetic value. These coatings are relied upon to ensure that the food or liquid inside the container are not contaminated by any metal by-products.

It would be desirable to have methods and systems capable of measuring the extent of cure of a coating that can easily be integrated into manufacturing operations to ensure proper protection and optimally infallible coverage of a coating on metal substrates. For containers that hold potentially corrosive material such as food or liquids, for example, it would be advantageous to know the extent of cure prior to filling the container with foodstuff. In addition to quality assurances, methods and systems for measuring the extent of cure at locations such as for example, immediately after exposure to elevated temperature, can help a manufacturing process operate efficiently to reduce defective materials and provide higher yields.

BRIEF DESCRIPTION OF THE DRAWINGS

FIG. 1 is a schematic depicting an embodiment of a spectroscopic apparatus positioned within a cylindrical container.

FIG. 2 is a schematic depicting another embodiment of a spectroscopic apparatus positioned within a cylindrical container.

FIG. 3 is a schematic depicting yet another embodiment of a spectroscopic apparatus positioned inside a cylindrical container.

SUMMARY

Figure 4:
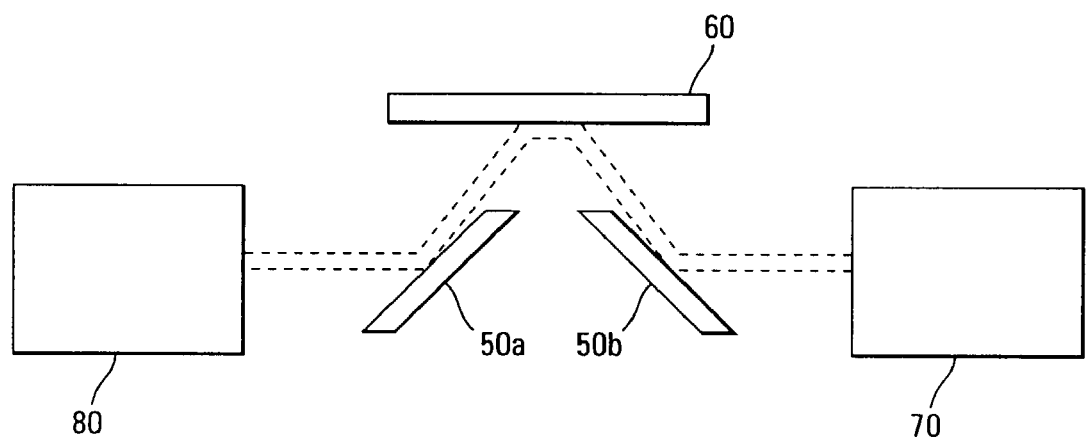
FIG. 4 is a schematic depicting an exemplary investigative apparatus positioned near a sample.

In one aspect of the invention, a method for measuring the extent of cure of a coating is provided which comprises the steps of i) operating a substrate coating operation (preferably a metal-containing substrate coating operation) to provide a coated substrate; ii) positioning an investigative apparatus near the coated substrate; and iii) operating the investigative apparatus to obtain an extent of cure reading, the reading preferably corresponding to an area on the coated metal-containing substrate. Optionally, the investigative apparatus can be connected to communicate with a data analysis system. To take advantage of a data analysis system, a preferred method of the invention includes a step of correlating output from the data analysis system to a process variable on the coating operation and adjusting the variable, if necessary.

In a further aspect of the invention, a method for monitoring a substrate (preferably a substrate metal-containing substrate) manufacturing operation includes the steps of: a) establishing an acceptable range for at least one output characteristic of the substrate; b) retrieving at least one value corresponding to the at least one output characteristic; c) analyzing the information; and d) identifying areas on the substrate having a value of the at least one output characteristic lying outside the acceptable range.

Still a further aspect of the invention is a system for monitoring a coating operation comprising: a spectroscopic probe positioned near a coated substrate (e.g. a metal-containing substrate); a spectrophotometer connected to the spectroscopic probe; and a data processing unit connected to the spectrophotometer.

As used herein and in the claims, "cure" and all tenses of the word is defined as the formation of a coating, including but not limited to hardening through chemical crosslinking and/or physical crosslinking.

DETAILED DESCRIPTION OF THE PREFERRED EMBODIMENTS

The present invention provides a method for measuring the extent of cure of a coating applied to a substrate, preferably a metal-containing (e.g., all metal, or metallized) substrate. In one embodiment, a method using spectroscopic tools is provided, to take advantage of the reflectivity of a coated metal or metal-containing substrate.

Advantageously, a method of the invention, if desired, can be integrated with a coating operation to provide methods and systems that can be capable of real-time monitoring. Furthermore, these methods and systems can optionally be integrated with automated (computerized) or manual data retrieval and analysis systems. By automatically retrieving and analyzing extent of cure readings using, for example, a computerized processor, preferred methods of the invention may help to ensure timely response to any necessary equipment or process modifications. This can subsequently lead to obtaining higher quality of cured coatings and achieving higher production yields.

Practicing certain embodiments of the invention can advantageously optimize a metal coating operation by helping to avoid overcuring and undercuring. Overcuring a coating is generally undesirable due to the effects it can have on the cured coating. Defects such as cracks or discoloration can result from overcuring. Furthermore, undercuring a coating is also generally undesirable, as it can lead to a low performing coating. For example, a coating that is not fully cured can exhibit unacceptable hardness, color and protective capability. A container intended to hold a carbonated soda pop beverage, for instance, having an improperly cured coating would not provide sufficient protection to the metal from the acidity of the liquid. This can then lead to corrosion and/or oxidation, making the product defective and possibly contaminating the liquid inside.

In one embodiment, a method includes the steps of: (i) operating a coating operation for coating a substrate (e.g., a metal-containing substrate); (ii) positioning an investigative apparatus near the coated substrate; and (iii) operating the investigative apparatus to obtain an extent of cure readings, where each reading or value corresponds to a particular measurement or sample area on the coated substrate.

The coating operations upon which a method of the invention can be practiced may include any of the known coating operations used in the art. For example, it is contemplated that a method can be performed on manufacturing lines that apply curable coating(s) onto pre-formed or pre-drawn container shapes. Alternatively, a methods of the invention can be used to measure characteristics of a coating that had been applied to substrates that are substantially planar, such as those in sheet form, or coils (rolls) that are unrolled prior to coating. Polymeric resins are generally applied to substrates using a variety of methods including coating by spray, dip, spin, powder, hand and curtain method.

Preferred apparatuses that may be used in the methods of the invention include a variety of diagnostic/analytical tools and equipment capable of investigating and retrieving data that can be directly or indirectly correlated to characteristics of a coating sample (e.g. area on the substrate). A preferred class of diagnostic tools suitable for the practice of the invention are those based on spectroscopic technology. Spectroscopic techniques useful for the invention include for example, infra-red spectroscopy (IR, mid-IR, near-IR, Fourier Transmission Infra-Red Spectroscopy (FTIR), etc) and Raman spectroscopy.

Fourier Transform Infrared Spectroscopy (FTIR) is an exemplary instrument and technique for analyzing and quantifying general classifications of unknown materials. It provides a unique fingerprint useful in the identification of a wide variety of chemicals. In practice, infrared wavelengths can be absorbed in a sample by the bonds that exist between the atoms; absorbance of the wavelengths can then be measured and plotted as a function of a wavelength. Since each chemical material has its unique arrangement of atoms and bonds, its absorbancies can be distinguished from other chemicals in the product. For example, functional groups such as carbonyls, amines, alcohols, nitro groups, and isocyanates each have characteristic absorbencies.

FTIR can be used to study curing, crosslinking, weathering and reaction rates. It can be a valuable tool for analyzing reaction kinetics, hydrogen bonding, dipolar attractions, solute-solvent interactions and the nature of inorganic resins at various temperatures. FTIR can produce a spectrum with good precision and reproducibility. A sample can be measured as an interferofram, digitized, and the spectrum calculated by a computer using the Fourier transform. This creates a spectrum in digital form which can be stored and retrieved without a substantial loss in precision or integrity. The computer executes a number of mathematical operations, such as smoothing, base line correction, scale expan sion, peak height, and area quantitation. Advantageously, FTIR is capable of subtracting one spectrum from another. By having this ability, FTIR can therefore be used to perform separations which may not be possible if performed chemically. For example, portions of a complex mixture can be subtracted from others to isolate the components of interest. Search algorithms can be used to retrieve the best matches from a spectral library database. This enables the analyst to identify a chemical or trade name. Preferred suppliers of FTIR instruments include Perkin Elmer (Boston, Mass.), ThermoElectron Corp. (Waltham, Mass.), Bruker Optik (Leipzig, Germany).

Other spectroscopic analysis tools that may be suitable for measuring the extent of cure of a coating include ultraviolet (UV) and visible light (VIS) probes and instruments. Ultraviolet and visible spectroscopy (UV/VIS) can examine how much a coating absorbs UV and visible wavelengths of light. UV/VIS is often used for quantitative measurements. Coatings that contain for example, aromatic rings such as polystyrene, alkyd resins, and many paint additives absorb UV light and can therefore be monitored for extent of cure. Colored materials can absorb light in the visible region of the spectrum. There are however, certain coatings that may neither absorb light in the UV nor the visible region. In such cases, the extent of cure can be measured by introducing an absorbing reagent. UV/VIS can also be used to determine amounts of certain compounds (e.g. formaldehyde) that exist in crosslinking resins. Preferred suppliers for UV-VIS instrumentation include Perkin Elmer (Boston, Mass.), Bruker Optik (Leipzig, Germany), and Ocean Optics, Inc. (Dunedin, Fla.).

Yet another spectroscopic investigative technique that may be used in the methods of the invention is nuclear magnetic resonance (NMR). In general terms, NMR can provide a fingerprint for a molecule. Further qualitative analysis and data that NMR can provide include for example, information about a chemical type, the number of atoms and the molecular configuration and conformation. NMR can also be useful to detect impurities and also as a quantitative tool.

Alternatively, the investigative apparatus used in certain embodiments of the invention can include tools capable of measuring "hardness" of a coating. Investigative tools that may be suitable include for example, mechanical testing apparatuses such as mechanical stress or pressure transducers. Hardness tests useful for the invention include Vickers, Knoop, Rockwell and Brinell. Preferred suppliers for hardness testing equipment are Microphotonics, Inc. (Allentown, Pa.), RDP Howden (Lemington Spa, UK) and New Age Testing Instruments (Southhampton, Pa.).

As further alternatives for investigative apparatuses to measure a coating's characteristics, those involving dielectric and acoustical probes can be used. Dielectric and acoustic tests which use electrical and sound waves, respectively, can measure how fast, and how far the corresponding waves travel through the coating, thus correlating to how thick or hard a coating is. These types of tests can advantageously be integrated on-line into a coating operation. A preferred supplier for dielectric apparatuses include for example, Hewlett-Packard Agilent Division (Palo Alto, Calif.).

Other classes of investigative apparatus that can provide extent of cure measurements include, for example, thermal techniques, chromatographic techniques, surface energy analysis, and color tests.

A preferred thermal technique is Differential Scanning Calorimetry (DSC). DSC can measure the difference between heat flow in a sample and a reference, under controlled thermal conditions. Coatings generally possess one or more characteristic transitions, including (1) the glass transition (Tg) or a transition related to changes in specific heat; (2) exothermic peaks brought about by a physical process or a chemical reaction such as crystallization or a chemical process such as a crosslinking reaction; (3) narrow endothermic peaks related to fusion or melting; (4) broader endothermic peaks caused by the volatilization of low-molecular-weight materials, dissociation, or decomposition; and finally, (5) an increase or decrease in heat flow with oxidative or thermal decomposition. Although DSC is primarily used for Tg determination and reaction kinetics analysis, the techniques may be useful in analyzing melting points, phase transition temperatures, and thermal stability. DSC techniques are particularly useful in determining the characteristics of a coating that undergoes crystallization when forming a hardened coating. Preferred suppliers for DSC apparatus include, for example, Perkin Elmer (Boston, Mass.) and TA Instruments (New Castle, Del.).

Within the class of thermal techniques also lie apparatuses that use thermal radiation. In these types of apparatuses, a probe can be used to measure the ambient heat intensity near the surface of a coating. Preferred suppliers of thermal radiation apparatuses include Indico (Edmonton, AB, Canada).

Chromatographic methods include investigative apparatuses that are able to measure retained solvents, using for example, gas chromatography (GC). GC is useful in identifying and quantifying solvents in various types of cured coatings, resins, and raw materials. It is often used to analyze the purity and composition of solvents. GC techniques, for example, can quantify amounts of coalescent agents in polymeric materials and identify residual monomers (after volatilization). Advantageously, it can be performed using a fairly small amount of sample, such as only about one microliter of solution after conducting a pyrolysis process.

Headspace analysis, also known as headspace gas chromatography/mass spectrometry (HGCMS), is a preferred chromatographic tool. It can be used to identify components emitted from a coating upon cure. For example, formaldehyde can be released upon curing a melamine-based coating. These types of investigative systems are also useful in identifying odors associated with certain coatings or in cases where a coating sample cannot be diluted with a solvent. Furthermore, headspace analysis can be used to identify and quantify residual solvents and monomers present in, for example, a paint film. Preferred suppliers of GC and HGCMS equipment include Hewlett Packard and Perkin Elmer (Boston, Mass.).

Liquid chromatography (LC) is another useful technique for indirectly measuring the extent of cure of a coating. LC can be used to identify and quantify, for example, low-level additives in compositions such as paints and coatings. Generally, this technique is used for extracts of such compositions. Additives that can be detected and quantified include, for example, antioxidants and rust inhibitors in E-Coat tanks, UV stabilizers, or other low-level additives. Various detectors (e.g., UV and fluorescence) can be used in association with the chromatography column to differentiate various components. Preferred suppliers of LC apparatuses include for example, Perkin Elmer (Boston, Mass.), and ThermoElectron Corp. (Waltham, Mass.).

Surface energy analysis can provide information that corresponds to the coating's ability to "wet" the substrate. This wetting ability, in turn, can be correlated to the extent of cure of a coating because surface energy drops as the amount of unreacted functionality of a coating decreases (e.g., as the amount of hydroxyls decrease, so does surface energy). It may useful to correlate wettability to a coating's known cure profile. Advanced Surface Technologies Inc. (Bellerica, Mass.) and KSV Instruments (Helsinki, Finland) are preferred suppliers of surface energy analysis systems.

Color tests can be performed using an optical probe that looks at sample areas on the substrate in a dark environment—one without ambient light effects (e.g. a dark booth or light sealed chamber). ASTM # D 2244-93 provides a procedure that may be used to measure color and calculate color differences. Color probes are commercially available from suppliers such as Hunter Associates Labs (Reston, Va.), Color Metrix (Sussex, Wis.) and Ocean Optics, (Dunedin, Fla.). A measured color can be correlated to the extent of cure of a coating by various ways. For example, increased yellowing can indicate phenolic condensation; dyes absorbed into a coating can be quantified and correlated to the extent of cure, and blackness or charring would be indicative of over-curing.

Out of the various investigative apparatuses, it is of particular interest in certain embodiments of the invention to utilize spectroscopic techniques such as by IR and Raman. Spectroscopic techniques generally are non-contact methods and are non-destructive to the sample and are can therefore be advantageously integrated into manufacturing operations to provide on-line or real-time monitoring.

Yet another class of investigative apparatuses useful for preferred methods of the invention include those that test the performance of the coating. This class of measurement systems include, for example, solvent rubs, bend tests, conductivity, process resistance, dynamic mechanical analysis (DMA) and extraction tests. A contacting device such as, for example, an INSTRON instrument can be used to determine coating performance characteristics such as tensile strength, elongation and other physical properties of various types of cured (e.g. dry) coatings. "Solvent rubs" can indicate the durability or extent of cure of a coating. A preferred procedure is outlined in ASTM# D 5402-93. For "bend testing," a preferred method is ASTM# E290-97a. Process resistance tests (those that assess how a coating will respond to processing such as pasteurizing or soaking) such as, for example, those that observe blush, adhesion failure, and blistering, can be used to characterize a coating. Still other tests may be those that can identify whether, for example, the contents of a metal container have been contaminated (e.g. metal compounds).

In preferred methods, the system used to measure the extent of cure uses spectroscopic techniques. Preferably, the investigative apparatus is a spectroscopic probe positioned at an angle relative to a measurement area or sample, where the angle is sufficient to provide an extent of cure reading. In particular, preferable methods utilize a spectroscopic probe, positioned to have an angle of about 90 degrees perpendicular to the area of measurement. However, it has been found that the metal in the metal-containing substrate can allow some flexibility in the angle at which a probe is positioned, as compared to substrates that do not possess reflectivity. Thus, the angle of a spectroscopic probe can even be between about 1 degree to about 45 degrees perpendicular to the area of measurement. Surprisingly, an angle of between about 1 degree to about 30 degrees perpendicular to the area of measurement, can be used.

Referring now to FIG. 1, one embodiment of a how a spectroscopic probe 20 can be positioned within a cylindrical container 10 is shown. Probe 20 can be used in this fashion to obtain, for example, an extent of cure reading from a coated sample area 5, located at the "dome" or bottom of a container. Probe 20 preferably contains both a photo source and detector. FIG. 2 provides another embodiment of an investigative apparatus setup useful in the methods of the invention. As seen in FIG. 2, probe 30 provides a plurality of source/detector combinations and can be capable of obtaining more than one reading, such as the extent of cure, at areas 15a and 15b of the sidewalls of container 10. As an alternative, a probe 40 such as that shown in FIG. 3 can be positioned within a container 10 to measure the extent of cure of target site or area 45. As seen in FIG. 3, probe 40 can be configured to have a photo source 47 and a detector 48 separate from each other, but still within the confines of probe 40.

In the scenarios where a coated substrate 60 is substantially planar, an investigative apparatus can be set up as shown in FIG. 4. In FIG. 4, an exemplary system is shown, utilizing mirrors 50a, 50b along with separate source 70 and detector 80 equipment that can be positioned adjacent a sample. Waves emitted from source 70 can be reflected onto a coated area on sample 60 and subsequently reflected back towards detector 80. Optionally, data retrieval, analysis, and/or storage systems can be connected to the investigative apparatus to achieve partial or complete automation of data management. This may be advantageous when the investigative apparatus is set up to communicate directly with process controllers installed within the coating operation, or provide alerts to an operator to respond to data retrieved by the apparatus. Investigative systems that are implemented in-line with the coating operation are preferably capable of quick retrieval and response.

The location of the investigative apparatus can be anywhere within the coating operation line or be positioned off-line, in a separate facility or in an area within close proximity of the coating line. The actual placement of the apparatus would likely depend on the needs of the user, and the type of investigative apparatus used—whether it would be feasible to place it in-line or necessitate installation off-line. An apparatus' location can also depend on how well or easy it is to present a coating sample. For example, spectroscopic tools can be used in-line, as the apparatus can include an optical probe capable of "looking" inside a formed substrate such as a can while it is on the manufacturing line (e.g., on a conveyor), and does not necessitate the need to remove the coating from the substrate for analysis. In coating operations that can incorporate investigative systems on-line, it may be advantageous to assess the cured coating immediately following the coating's exposure to elevated temperature, such as an oven. Alternatively, a sample can be obtained from the end of the line to check the coating upon complete processing. Optionally the coating can be measured or assessed at two or more stations in a manufacturing line.

In other types of investigative apparatuses, those that can be placed into a class of "destructive tests," the coating may need to be, for example, removed or extracted, from its substrate. This is such the case for apparatuses used in several of the chromatographic techniques. Other types of destructive yet useful tests include those that may sacrifice the sample. For example, a "metal exposure test" can be used to assess a coating. In this type of performance test, a formed metal substrate such as a container is filled with a salt solution; an electrode is then positioned on the interior of the container, and another on the exterior; a low voltage (about 5V) current is subsequently applied. The conductivity of current flow is measured and indicates the "barrier properties"; e.g., where sufficient cure can indicate better barrier properties. After undergoing a metal exposure test, the sample may no longer be used for its original purpose, other than being a representative of the coated substrates made along with it. Another analysis tool would be a hardness test, where an apparatus that is capable of making physical contact is placed near the sample and then made to contact a point on the sample with a certain amount of force. Such a contact can leave an imperfection, sometimes even a crack, in the film coating and therefore sacrifices the sample, since the imperfection can lead to substrate corrosion or contamination from undesirable compounds extracted from the coating.

To implement "destructive" tests in a coating operation, a diverting process can be used. For example, one sample out of every pre-determined number or group (e.g., 100, 250, 1000, etc) can be diverted away from the coating line to an off-line test station. The sampling size and strategy is preferably determined using statistical tools that can address the needs of the operation and level of monitoring desired. The diverting process can be performed in a variety of known methods including for example, diversion conveyors or manual pulls (e.g., operator removes the sample from the operation line).

If desired, off-line sampling may also be used for non-destructive tests. The use of off-line testing is generally used to avoid negatively impacting an operation or machine speed. Where off-line testing methods are incorporated, the results of any analysis can optionally be fed back to the process manually or automatically by inputting results into an data analysis & storage system.

Figure 5:
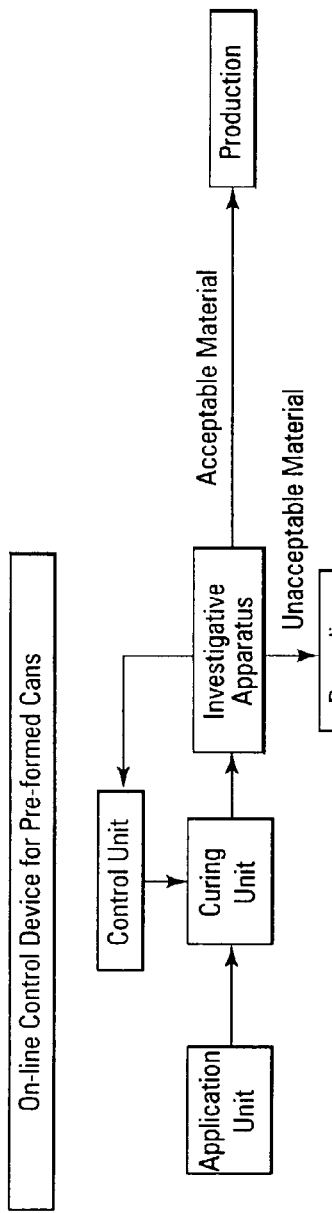
FIG. 5 is a flowchart of a process having an investigative apparatus on-line with a coating operation.
Figure 6:
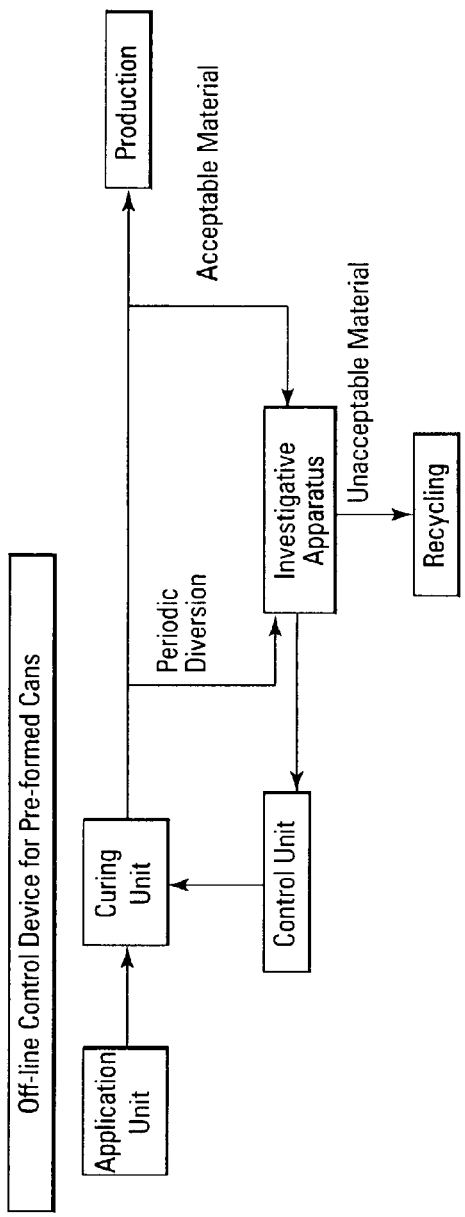
FIG. 6 is a flowchart of a process having an investigative apparatus off-line.

FIGS. 5 and 6 provide exemplary flow charts of process steps for certain methods of the invention. FIG. 5 depicts a process that has the investigative apparatus on-line within the coating operation and utilizes an optional control unit that can process or store data retrieved by the investigative apparatus. Alternatively, the investigative apparatus can be placed off-line from the coating operation and be fed samples through a diversion process, as shown in FIG. 6. If desired, more than one investigative apparatus or test stations can be incorporated into an operation.

A general class of coatings that are preferably monitored and measured using the methods of the invention are thermoset coatings that can be cured using heat and/or radiation (UV, VIS, and IR range). Suitable coatings that can be monitored include, for example, acrylics, polyesters, urethanes, polyureas, epoxies and combinations thereof. Coatings having at least one chemically reactive functionality such as an acid, an amine, a hydroxyl an isocyanate and a UV-curable moiety are also suitable for the methods of the invention.

Another class of coatings that can be assessed include thermoplastic materials that have been modified with an additive or taggant to provide a detectable chemical reaction. By introducing a taggant to a thermoplastic material, a traceable quantity of energy input, as a result of the "tagging reaction" can be measured. Advantageously, increased branching can help lead to lower curing temperatures or dwell times in various systems. Although not wishing to be bound by theory, it is believed this advantage can occur since the same number of physical cross-links can be achieved in a more rapid rate than without the taggant.

A taggant can be in the form of a polymeric additive having a functionality that can react with a core resin of a coating. One type of additive, for example, is a mono-functional polymeric material. Use of a mono-functional polymeric additive provides a reaction that creates chemical branching that can increase the number of physical cross-links, but does not form the chemically cross-linked network apparent in thermoset materials. Suitable additives can vary, depending on the actual chemistry of a coating. In particular, additives having a functionality such as for example, a hydroxyl, an acid, an amine, or an isocyanate, can be used. Preferably, the additive is non-toxic if used in the food and beverage packaging industry. A particularly preferred additive for such uses would have a molecular weight greater than about 1000 Daltons.

It is preferred that a sufficient number of samples or measurements are taken for analysis. By taking a series of samples or measurements, a profile of a certain portion of the coating substrate can be obtained if desired. Alternatively, it may be desirable to identify from the samples, the area on the substrate that has the lowest value of the extent of cure. Taking a 'moving average' such as by measuring coating characteristics of a series of units and averaging the values can be advantageous when assessing how well a coating process is performing.

In a one-piece can (e.g., drawn container) such as, for example, an unfilled soda pop can, at least three measurement areas are preferably measured: an area on the top half of the cylinder, an area on the bottom half of the cylinder, and an area on or about the center of the bottom of the can. More measurements on more areas on the can could, of course, provide greater accuracy of the values or a broader profile, however the benefit of increasing the number of samples is preferably balanced against the interests of ensuring line speed, preferably without compromising quality of the units.

In the instances where sheets or coils (e.g. rolls) are coated and manufactured, samples are preferably taken in the direction transverse to the machine direction, (i.e., across the sheet or roll) and repeated at certain intervals or distances along the line direction. At least one area can be measured for extent of cure; preferably, at least three areas within the transverse direction on the sheet or roll is sampled and measured. It may be desirable to take numerous samples in the transverse direction, to provide a profile (cure v. location). This may, if desired, be achieved by mounting one or more detectors on an apparatus that moves relative to the substrate in the transverse direction.

Preferred substrates for the methods of the invention include metal containing substrates, which can be for example, metal itself, or metal coated or metallized plastic, paper, polymeric films, wood or combinations thereof. Sizes of formed (shaped) substrates can vary quite broadly, from small thimble-size cans to enormous rail cars or truck tankers (e.g., milk tank). The sizes and number of investigative apparatuses such as the probes involved in the apparatuses is preferably adjusted according to the size of a sample.

Optionally, extent of cure monitoring systems can be partially or fully integrated into coating operations and provide quick response to potential defect-causing scenarios. This can be performed by providing extent of cure data to a system that can subsequently alert or actually modify a process variable of the coating operation. This may require further process equipment that is able to communicate and control the process.

Variables that can affect the extent of cure or formation of a coating, (as well as other coating characteristics) and are therefore preferably capable of modification include, for example, machine temperature and pressure (including varying different zones); line speed; soak/bake order, duration or dwell time in soak/bake; coating thickness (premetered) by controlling roller settings: gap, speed, sheet feed rate or by controlling spray variables: spray volume, air flow and spray pattern; oven flow rate (for air or gas flow through oven); flow gas composition; water/air quench; geometry of energy output such as wattage (for UV or IR cure); energy wavelength such as filament type (for UV or IR cure); and metal thickness.

A cured or formed coating can be analyzed for various chemical and/or performance characteristics. These characteristics could directly or indirectly provide information on how well a coating operation is working and possibly predict how well a coating would perform under certain conditions. Coating characteristics that can be measured using the tools described above include, for example, mechanical modulus, hardness and extent of cure. Of these, the extent of cure is a preferred characteristic to be measured, as it can be quantified and assessed in-line, quickly.

Generally, the degree of cure is provided as a value calculated as a ratio. Each type of coating has a certain acceptable range, generally determined by studying the chemistry of the coating and its known characteristics. A cure profile, for example, is one tool useful in characterizing the extent of cure of a coating.

For the "0%" cure value which would indicate an uncured coating, an exemplary method includes: taking a wet coating (coated onto a metal-containing substrate) and drying it at room temperature for a period sufficient to remove substantially all carriers but without initiating any chemical reactions, if applicable (e.g. thermoset compositions). The amount of reacted functionalities as well as the amount of unreacted functionalities is then measured, using for example, spectroscopy. The ratio of reacted functionalities over unreacted functionalities is then calculated to give the "0%" or lowest value for the extent of cure. The upper limit of how cured a coating can be would be the highest or "100%" value. One way to determine this maximum cure is by curing the coating for a time period that is at least about triple the "normal" time it takes to cure the coating under normal conditions or a time period just short of initiating thermal degradation of the coating. For example, a coating on a coil or sheet has a normal bake time of about 8 to about 20 seconds at 232.2° C. to about 371.1° C. To obtain the maximum cure, a similar sample is baked for 60 seconds or more at about 232.2° C. to about 371.1° C. The ratio of reacted functionalities is obtained for both points. For substantially planar coated metal-containing substrates, the following guidelines are preferably followed: coated sheets are cured at about 176.7° C. to about 232.2° C. for about 8 to 10 minutes for the minimum extent of cure ratio; for maximum cure, a similar sheet is cured at the same temperature for about 30 minutes; coatings on formed metal-containing substrates such as containers or cylinders are cured at 148.9° C. to about 260.0° C. for about 3 to about 50 minutes to obtain minimum extent of cure; for maximum cure, a similar coated formed substrate is cured for at the same temperature for about 15 minutes.

A number of embodiments of the invention have been described. Nevertheless, it will be understood that various modifications may be made without departing from the spirit and scope of the invention. Accordingly, other embodiments are within the scope of the following claims.

EXAMPLES

Example 1

355 mL two-piece beverage cans were coated with an epoxy acrylate polymeric coating and cured in a two-zone oven using a variety of different oven conditions in order to determine the lowest oven temperature and dwell time capable of producing sufficient cure in each can, thereby optimizing the process for both cost and performance. The first zone of the oven was held constant at 171.1° C., while the temperature of the second zone and the oven dwell time (controlled by the speed of the oven belt) were varied according to the conditions set forth in Table 1.

TABLE 1

| Condition | Zone 2 Temp (° C.) | Dwell Time (s) |
|---|---|---|
| A | 185.6 | 106 |
| B | 185.6 | 166 |
| C | 201.1 | 106 |
| D | 201.1 | 166 |
| E | 182.2 | 136 |
| F | 204.4 | 136 |
| G | 193.3 | 101 |
| H | 193.3 | 180 |
| I | 193.3 | 136 |

The performance of each can was evaluated by the following tests:
  a) 1% Joy™ Dishwashing Liquid/water pasteurization at 100.0° C. for 15 minutes;
  b) Gatorade™ test, hot filled and held for 20 minutes at 85.0° C.;
  c) 3% acetic acid/water test for 15 minutes at 100.0° C.;
  d) Bend testing according to ASTM E290-97a;
  e) Water flavor testing after 30 minutes at 82.2° C., followed by cooling overnight at room temperature; and
  f) Drop Metal Damage Test: Drop metal damage testing consists of measuring the metal exposure (ME) of a can, filling it with water, dropping the can from a height of 81.3 cm onto an angled plane for both sides of the bottom of the can, and re-measuring the metal exposure. A "passing" score is defined as a difference of less than 5 mA. Two sets of twelve cans (Set One with surfactant, Set Two without) were tested for each bake condition.

With the exception of drop metal damage testing, results from all the other tests showed no significant difference between the bake conditions. Thus, drop metal damage testing was identified as the first mode of failure and was used to define the performance of the can. For the drop metal damage test, 5 bake conditions passed and 4 bake conditions failed (Conditions A, B, E and G—where ΔME was greater than 5 mA) as shown in the Table 2:

TABLE 2

| Condition | Zone 2 Temp (° C.) | Dwell Time (s) | Set 1 ΔME (mA) | Set 2 ΔME (mA) |
|---|---|---|---|---|
| A | 185.6 | 106 | 35.4 | 37.2 |
| B | 185.6 | 166 | 23.4 | 7.5 |
| C | 201.1 | 106 | 1.6 | 1.2 |
| D | 201.1 | 166 | 1.7 | 1.1 |
| E | 182.2 | 136 | 72.7 | 108.3 |
| F | 204.4 | 136 | 0.9 | 3.1 |
| G | 193.3 | 101 | 113.9 | 41.1 |
| H | 193.3 | 180 | 1.3 | 0.6 |
| I | 193.3 | 136 | 4.5 | 0.8 |

The extent of cure of each can was measured by cutting 2.54 cm×2.54 cm samples from a number of locations on the can using metal shears and evaluated by:
  a) Glass transition temperature (Tg) by differential scanning calorimetry (DSC) using a Perkin Elmer DSC7;
  b) Fourier Transform infrared spectroscopy using a Perkin Elmer Spectrum 2000 FTIR in specular reflectance geometry; and
  c) L, a, b color analysis by reacting the coating with bromophenyl blue dye for 1 minute, rinsing with deionized water, and analyzing with a Hunter Labs ColorQUEST machine. This dye reacts with the remaining unreacted functionality in the system, indicating a degree of cure. In this test, L represents the light/dark scale, a represents the red/ green scale, and b represents the blue/yellow scale.

Samples were cut from the upper, middle, and lower sidewalls; well area; and the dome area. The upper dome area of the can was found to be a potential problem area exhibiting low extent of cure due to increased coating thickness and low heat input; however, the different areas were found to trend up and down together, so the data from the upper sidewall was used.

Tg analysis by DSC showed no discernable difference between samples.

Fourier transform infrared spectroscopic analysis was used to analyze coating formation (cure) by dividing the intensity of a peak representative of the cross-links by the intensity of a peak representative of the unreacted functionality in order to determine the cure ratio or cure number for each sample. This number is defined so that as cure increases, the cure ratio also increases. For each bake condition, the cure ratios were obtained and are tabulated in Table 3.

TABLE 3

| Condition | Zone 2 Temp (° C.) | Dwell Time (s) | Set 1 Cure Ratio | Set 2 Cure Ratio |
|---|---|---|---|---|
| A | 185.6 | 106 | 0.80 | 0.85 |
| B | 185.6 | 166 | 0.89 | 1.03 |
| C | 201.1 | 106 | 1.23 | 1.53 |
| D | 201.1 | 166 | 1.63 | 1.44 |
| E | 182.2 | 136 | 0.89 | 0.96 |
| F | 204.4 | 136 | 1.35 | 1.95 |
| G | 193.3 | 101 | 0.92 | 0.92 |
| H | 193.3 | 180 | 1.19 | 1.70 |
| I | 193.3 | 136 | 1.02 | 1.24 |

Figure 7:
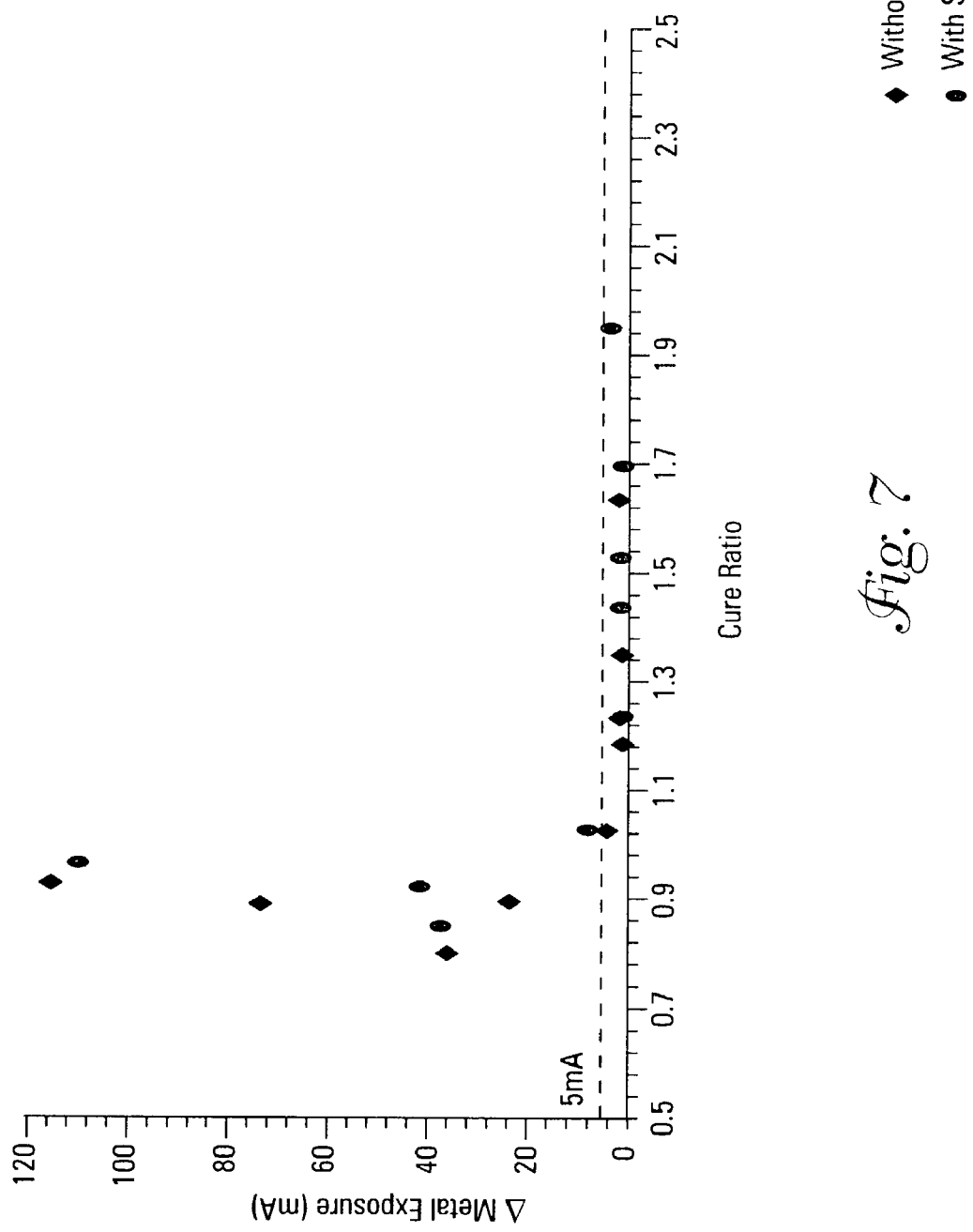
FIG. 7 is a graph depicting the results from Example 1.

The cure ratio was compared directly to the average ΔME value for each bake condition. See FIG. 7.

It was apparent that "failure" or unacceptable cure" began at a cure ratio below 1.1. Using this diagram (FIG. 7), it became possible to optimize and control the system by modifying bake time and temperature in a recursive fashion.

Figure 8:
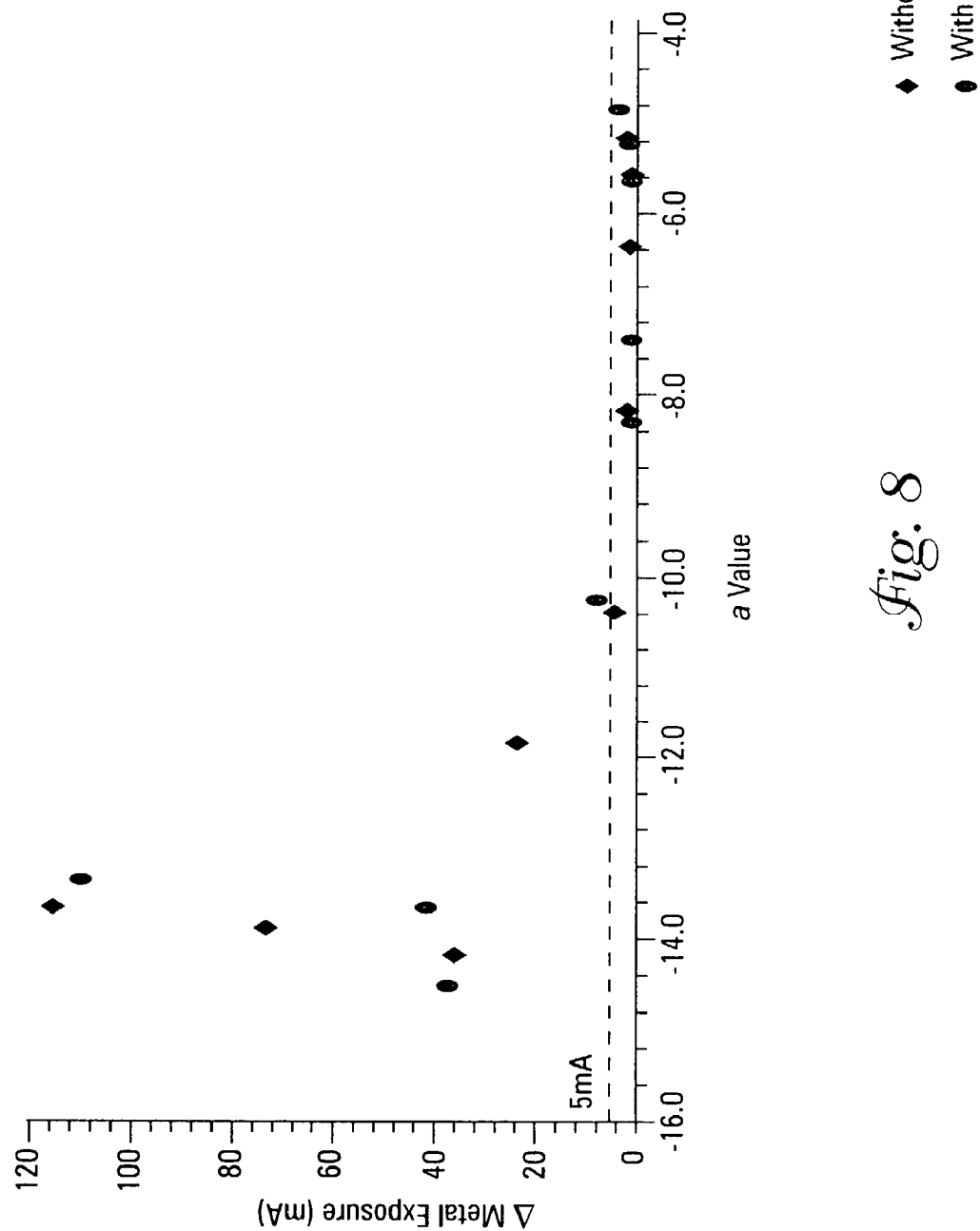
FIG. 8 is a graph depicting color analysis data obtained in Example 1.

Color analysis was used to analyze cure by quantifying the color imparted from the bromophenyl blue dye soak and comparing it to the performance of each can. Both the L and the a values correlated well with the drop damage performance, but the b values did not (the sample actually turned green rather than blue as it reacted with the dye). The a values for both sets of cans are shown in Table 4, and their correlation with the drop metal damage results are shown in FIG. 8.

TABLE 4

| Condition | Zone 2 Temp (° F.) | Dwell Time (s) | Set 1 a Value | Set 2 a Value |
|---|---|---|---|---|
| A | 185.6 | 106 | −14.15 | −14.48 |
| B | 185.6 | 166 | −11.86 | −10.23 |
| C | 201.1 | 106 | −8.17 | −7.39 |
| D | 201.1 | 166 | −5.14 | −5.22 |
| E | 182.2 | 136 | −13.88 | −13.36 |
| F | 204.4 | 136 | −5.57 | −4.84 |
| G | 193.3 | 101 | −13.66 | −13.65 |
| H | 193.3 | 180 | −6.36 | −5.65 |
| I | 193.3 | 136 | −10.39 | −8.26 |

Similar to the results obtained using FTIR, failure was found to occur as the a value moves below −10, indicating a stronger green color as a result of dye absorption. Again, this diagram can be used to optimize control the system by modifying bake time and temperature in a recursive fashion.

Example 2

Aluminum coils were coated with a primarily thermoplastic coating made having epoxy melamine, using a variety of line speeds, coating weights, and peak metal temperatures (PMT's). The parameters for each of the coils are provided in Table 5.

TABLE 5

| Coil | Line Speed (m/min) | Coating Weight (g/m$^2$) | PMT (° C.) |
|---|---|---|---|
| A | 38.1 | 12.40 | 232.2 |
| B | 38.1 | 11.93 | 248.9 |
| C | 56.4 | 11.93 | 215.6 |
| D | 56.4 | 11.93 | 248.9 |
| E | 61.0 | 12.55 | 215.6 |
| F | 61.0 | 12.40 | 248.9 |
| G | 61.0 | 14.88 | 215.6 |
| H | 61.0 | 12.09 | 215.6 |
| I | 38.1 | 12.71 | 248.9 |
| J | 38.1 | 11.47 | 215.6 |
| K | 38.1 | 12.24 | 232.2 |
| L | 38.1 | 12.86 | 248.9 |
| M | 56.4 | 12.40 | 215.6 |
| N | 61.0 | 13.95 | 215.6 |
| S | 61.0 | 13.17 | 215.6 |
| T | 8.1 | 13.02 | 248.9 |

The coatings of each coil were evaluated for extent of coating formation by measuring the retained butanol in the system using Gas Chromatography/Headspace Analysis (GC/HS) (HP 5890 Series II) and Fourier Transform Infrared Spectroscopy (FTIR) (Perkin Elmer Spectrum 2000). Because the cross-linker in this system was blocked with butanol, measuring the amount of retained butanol provided a correlation as to how many potential cross-links had de-blocked and reacted. As this coating was primarily thermoplastic, a retained butanol value below 50 mg/basebox was considered to indicate sufficient energy input for adequate coating performance. (One basebox is equal to 20.23 m$^2$)

Figure 9:
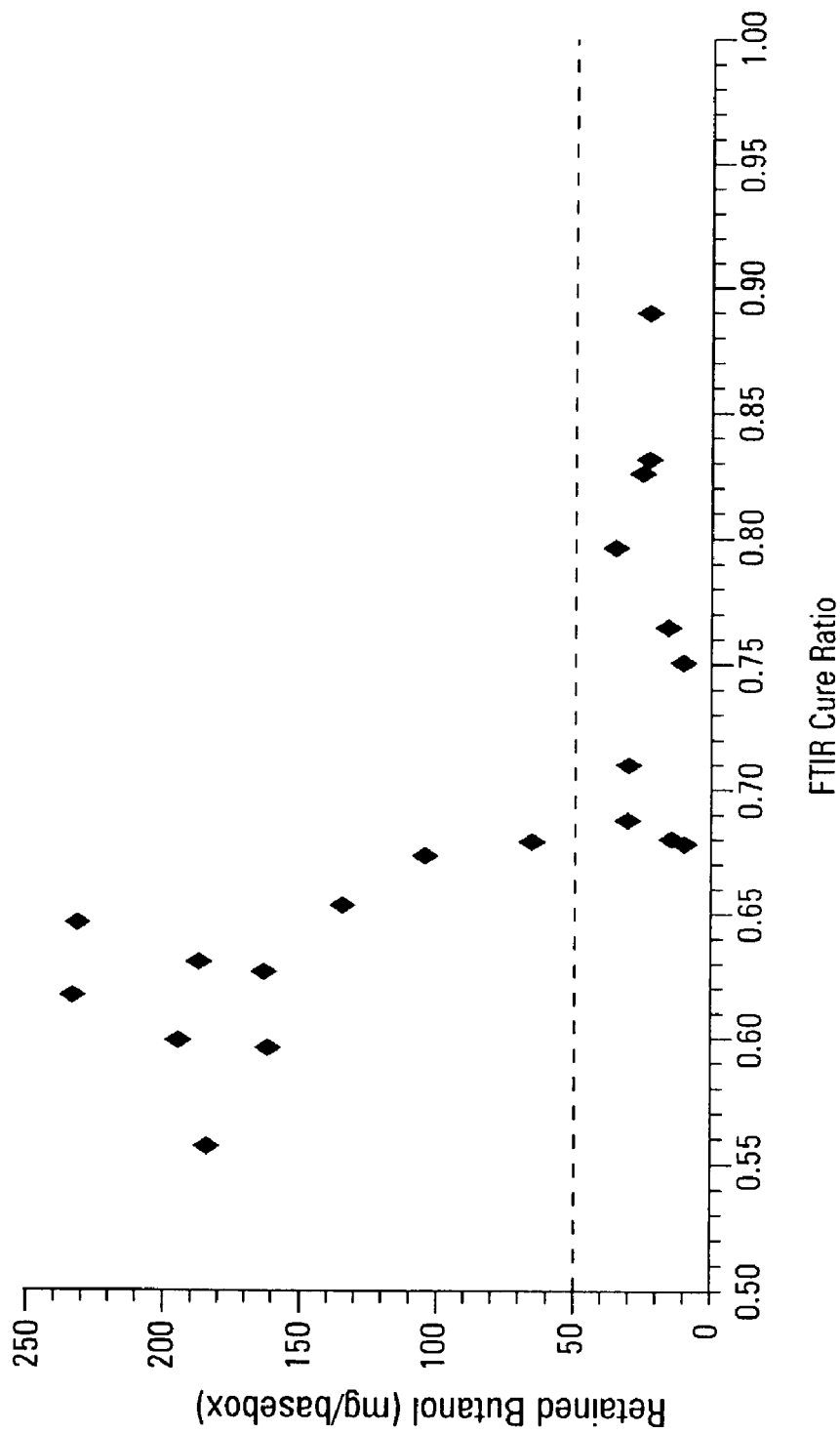
FIG. 9 is a graph depicting the results from Example 2.

FTIR was used to analyze cure (coating formation) by dividing the intensity of a peak representative of the cross-links by the intensity of a peak representative of the unreacted functionality in order to determine the cure ratio or cure number for each coil. These values are shown in the Table 6 and FIG. 9.

TABLE 6

| Coil | Retained Butanol (mg/basebox) | Cure Ratio |
|---|---|---|
| A | 26 | 0.83 |
| B | 10 | 0.68 |
| C | 194 | 0.60 |
| D | 25 | 0.89 |
| E | 163 | 0.63 |
| F | 31 | 0.71 |
| G | 233 | 0.61 |
| H | 135 | 0.65 |
| I | 11 | 0.75 |
| J | 106 | 0.67 |
| K | 37 | 0.80 |
| L | 17 | 0.77 |
| M | 231 | 0.64 |
| N | 25 | 0.83 |
| O | 184 | 0.56 |
| P | 66 | 0.68 |
| Q | 31 | 0.69 |
| R | 161 | 0.59 |
| S | 187 | 0.63 |
| T | 15 | 0.68 |

It is clear that failure in this system begins at a cure ratio below 0.70. Using this diagram it was possible to optimize the system by modifying line speed, coating weight, and peak metal temperature in a recursive fashion.

Example 3

A manufacturer applied an epoxy acrylate polymeric coating to the interior of two-piece beverage cans (12 oz., 355 mL) to provide a barrier between the product and the can material. The coating was cured in a commercial two-zone oven to achieve coating cure sufficient to provide an adequate barrier (as described in Example 1). At an unknown point in time, the manufacturer's oven malfunctioned and cooled to ambient temperature before being discovered, resulting in an indeterminate amount of cans with insufficient coating cure to provide an acceptable barrier.

A sampling of the coated cans was gathered from this manufacturing run. The cans were collected from lots produced at different times, beginning with cans produced at the last known time when the oven was at the proper elevated temperature (Time A in Table 7), and ending with cans produced just after the oven was noticed to be at ambient temperature (Time B in Table 7).

The cans were analyzed using Fourier Transform Infrared (FTIR) Spectroscopy as described in Example 1. Again, cure was analyzed by dividing the intensity of a peak representative of the cross-links by the intensity of a peak representative of the unreacted functionality in order to determine the cure ratio or cure number for each sample. This number is defined so that as cure increases, the cure ratio also increases. The cure ratios for each can are provided in Table 7.

TABLE 7

| Time | Oven Temperature | Cure Ratio |
| --- | --- | --- |
| A | Normal Operation | 2.12 |
| B | Unknown | 2.04 |
| C | Unknown | 2.00 |
| D | Unknown | 1.92 |
| E | Unknown | 1.02 |
| F | Ambient | 0.59 |

These values were compared to the failure point of 1.1 derived in Example 1. The cans produced prior to Time D were determined to be acceptable for use and released into general production. All cans produced after Time D were insufficiently cured and were recycled as a result.

These results demonstrate that a monitoring apparatus and method of the invention can be used to identify inadequately coated and/or cured pieces, e.g. upon the occurrence of a process interruption. When performed on-line and preferably in real-time, a monitoring apparatus and method according to certain embodiments of the invention can reduce or eliminate out-of-specification pieces. When performed after-the-fact, as described herein, a monitoring system can facilitate salvage of pieces and identify only those defective pieces that can be reworked.

Example 4

A manufacturer applied an epoxy acrylate polymeric coating to the interior of two-piece beverage cans (each 12 oz. or 355 mL) to provide a barrier between the product and the can material. The coating was cured in a commercial two-zone oven to achieve coating cure sufficient to provide an adequate barrier (as described in Example 1). To reduce operating costs, the manufacturer lowered the operating temperature of their oven.

Two sets of cans were gathered from the manufacturer's facility before and after the reduction in operating temperature. These cans were analyzed using Fourier Transform Infrared (FTIR) Spectroscopy as described in Example 1. Again, cure was analyzed by dividing the intensity of a peak representative of the cross-links by the intensity of a peak representative of the unreacted functionality in order to determine the cure ratio or cure number for each sample. This number is defined so that as cure increases, the cure ratio also increases. The cure ratios for each set of cans are shown in Table 8.

TABLE 8

| Can Set | Average Cure Ratio |
| --- | --- |
| Before Oven Change | 1.86 |
| After Oven Change | 1.79 |

These values were compared to the failure point of 1.1 derived in Example 1. The cans produced after the oven change were determined to be slightly less cured than those produced prior to the oven change, but still well above the identified failure point.

These results demonstrate that a monitoring apparatus and method according to an embodiment of the invention can be used to optimize the efficiency of a particular process line.

What is claimed is:

1. A method for measuring the extent of cure of a coating, comprising:

operating a coating operation to provide a coating on a metal-containing container;

selecting an area of the coating on the metal-containing container for analysis;

positioning a Fourier transform infrared spectroscopic probe near the area; and operating the probe to obtain an on-line extent of cure reading using Fourier transform infrared spectroscopy, wherein the extent of cure reading measures only chemical changes in the coating, and wherein the reading corresponds to the area on the coated metal-containing container.

2. The method according to claim 1, wherein the metal-containing container is a can.

3. The method according to claim 1, wherein the coating comprises a compound selected from a group consisting of acrylic, polyester, urethane, epoxy, polyurea and combinations thereof.

4. The method according to claim 1, wherein the coating comprises a chemically reative functionality selected from a group consisting of an acid, an amine, an isocyanate, a hydroxyl and a UV-curable moiety.

5. The method according to claim 1, wherein the metal-containing container is in the form of a cylinder having an open top, a side wall, and a bottom.

6. The method according to claim 1, further comprising:

repeating the steps of operating the investigative apparatus to obtain a plurality of extent of cure readings; and identifying the lowest reading from the plurality of extent of cure readings.

7. The method according to claim 1, wherein the spectroscopic probe is positioned at an angle relative to a measurement area, the angle being sufficient to provide an extent of cure reading.

8. The method according to claim 7, wherein the angle of the spectroscopic probe is about 90 degrees perpendicular to the area of measurement.

9. The method according to claim 7, wherein the angle of the spectroscopic probe is between about 1 degree to about 45 degrees perpendicular to the area of measurement.

10. The method according to claim 7, wherein the angle of the spectroscopic probe is between about 1 degree to about 30 degrees to the are of measurement.

11. The method according to claim 1, wherein the coating on the metal containing container comprises a taggant.

12. The method according to claim 1, wherein operating the investigative apparatus is performed after the coating on the metal-containing container hardens.

13. The method of claim 1, wherein operating the investigative apparatus is repeated to obtain a plurality of extent of cure readings.

14. The method of claim 13, further comprising:

obtaining a profile of the obtained extent of cure readings against the location of the measured area.

15. The method of claim 1, further comprising:

connecting the probe to a data analysis system; and communicating the extent of cure reading to the data analysis system.

16. The method of claim 15, further comprising:

obtaining at least one output from the data analysis system, wherein the output value is correlated to at least one process variable of the coating operation; and optionally adjusting the at least one process variable.

17. The method according to claim 16, wherein the at least one process variable is selected from a group consisting of dwell time, machine temperature, machine pressure, line speed, volumetric flow rate, flow gas composition, coating thickness, energy wavelength, energy intensity, spray pattern, and spray volume.

18. The method according to claim 16, wherein the steps are performed sequentially.

* * * * *